(12) United States Patent
Patcas et al.

(10) Patent No.: US 10,315,970 B2
(45) Date of Patent: Jun. 11, 2019

(54) CATALYST FOR DEHYDROGENATING HYDROCARBONS

(71) Applicant: BASF SE, Ludwigshafen (DE)

(72) Inventors: Florina C. Patcas, Ludwigshafen (DE); Bernd Hinrichsen, Stuttgart (DE); Martin Dieterle, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/309,029

(22) PCT Filed: May 6, 2015

(86) PCT No.: PCT/EP2015/059907
§ 371 (c)(1),
(2) Date: Nov. 4, 2016

(87) PCT Pub. No.: WO2015/169825
PCT Pub. Date: Nov. 12, 2015

(65) Prior Publication Data
US 2017/0121241 A1    May 4, 2017

(30) Foreign Application Priority Data
May 9, 2014   (EP) .................................... 14167665

(51) Int. Cl.
*C07C 5/333*        (2006.01)
*B01J 23/00*        (2006.01)
(Continued)

(52) U.S. Cl.
CPC ............ *C07C 5/3332* (2013.01); *B01J 23/002* (2013.01); *B01J 23/83* (2013.01); *B01J 23/8898* (2013.01);
(Continued)

(58) Field of Classification Search
CPC combination set(s) only.
See application file for complete search history.

(56) References Cited

U.S. PATENT DOCUMENTS

| 4,460,706 A | 7/1984 | Imanari et al. |
| 4,758,543 A | 7/1988 | Sherrod et al. |

(Continued)

FOREIGN PATENT DOCUMENTS

| CA | 2298227 A1 | 8/2000 |
| EP | 0181999 A1 | 5/1986 |

(Continued)

OTHER PUBLICATIONS

An English translation of Baier et al. (EP 1027928 A1) (Year: 2000).*

(Continued)

*Primary Examiner* — Jun Li
(74) *Attorney, Agent, or Firm* — Drinker Biddle & Reath LLP

(57) ABSTRACT

The present invention relates to a catalyst based on iron oxide for the dehydrogenation of hydrocarbons and also a process for producing it. The catalyst comprises at least one iron compound, at least one potassium compound and at least one cerium compound, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 20% by weight, based on the total catalyst, of the K/Fe mixed oxide phases and comprises crystalline cerium dioxide having a crystallite size in the range from 10 nm to 30 nm.

11 Claims, 1 Drawing Sheet

(51) Int. Cl.
- *B01J 37/04* (2006.01)
- *B01J 37/08* (2006.01)
- *B01J 23/83* (2006.01)
- *B01J 23/889* (2006.01)
- *B01J 35/02* (2006.01)
- B01J 35/00 (2006.01)
- B01J 35/10 (2006.01)
- B01J 37/00 (2006.01)

(52) U.S. Cl.
CPC ............... *B01J 35/02* (2013.01); *B01J 37/04* (2013.01); *B01J 37/08* (2013.01); *B01J 37/088* (2013.01); B01J 35/002 (2013.01); B01J 35/0006 (2013.01); B01J 35/023 (2013.01); B01J 35/1009 (2013.01); B01J 37/0009 (2013.01); B01J 2523/00 (2013.01); C07C 2523/04 (2013.01); C07C 2523/745 (2013.01); C07C 2523/83 (2013.01); C07C 2523/889 (2013.01)

(56) References Cited

U.S. PATENT DOCUMENTS

| | | | |
|---|---|---|---|
| 6,028,027 A | | 2/2000 | Baier et al. |
| 6,222,085 B1 * | | 4/2001 | Shiraki .................... B01J 23/78 |
| | | | 502/330 |
| 6,551,958 B1 | | 4/2003 | Baier et al. |
| 7,663,009 B2 | | 2/2010 | Kowaleski |
| 8,003,837 B2 * | | 8/2011 | Walsdorff ............... B01J 23/745 |
| | | | 502/336 |
| 2006/0106267 A1 * | | 5/2006 | Kowaleski ............... B01J 23/745 |
| | | | 585/444 |
| 2009/0062587 A1 * | | 3/2009 | Kowaleski ............... B01J 23/002 |
| | | | 585/654 |
| 2013/0165723 A1 | | 6/2013 | Patcas et al. |
| 2017/0073284 A1 * | | 3/2017 | Patcas .................... B01J 23/002 |

FOREIGN PATENT DOCUMENTS

| | | | |
|---|---|---|---|
| EP | 0894528 A2 | 2/1999 | |
| EP | 1027928 A1 * | 8/2000 | ............ B01J 23/745 |
| EP | 2106852 A1 | 10/2009 | |
| RU | 2302293 C1 | 7/2007 | |
| RU | 2325229 C1 | 5/2008 | |
| RU | 2385313 C2 | 3/2010 | |
| WO | WO-9710898 A1 | 3/1997 | |
| WO | WO-9949966 A1 | 10/1999 | |

OTHER PUBLICATIONS

Dulamiṭă, N., et al., "Ethylbenzene dehydrogenation on Fe2O3—Cr2O3—K2CO3 catalysts promoted with transitional metal oxides", Applied Catalysis A: General, vol. 287, No. 1, (2005), pp. 9-18.

Hirano, T., "Dehydrogenation of ethylbenzene over potassium-promoled iron oxide containing cerium and molybdenum oxides", Applied Catalysis, vol. 28, (1986), pp. 119-132.

International Search Report for PCT/EP2015/059907 dated Aug. 31, 2015.

International Search Report for PCT/EP2015/059908 dated Jul. 22, 2015.

Liao, S-J., et al., "Effecst of $TiO_2$ on the structure and catalytic behavior of iron-potassium oxide catalyst for dehydrogenation of ethylbenzene to styrene", Catalysis Communications, vol. 9, No. 9, (2008), pp. 1817-1821.

International Preliminary Report on Patentability for corresponding PCT/EP2015/059907 dated Nov. 15, 2016.

* cited by examiner

CATALYST FOR DEHYDROGENATING HYDROCARBONS

CROSS-REFERENCE TO RELATED APPLICATIONS

This application is a national stage application (under 35 U.S.C. § 371) of PCT/EP2015/059907, filed May 6, 2015, which claims benefit of European Application No. 14167665.0, filed May 9, 2014, both of which are incorporated herein by reference in their entirety.

The present invention relates to a catalyst based on iron oxide for the dehydrogenation of hydrocarbons and also a process for producing it. The catalyst comprises at least one iron compound, at least one potassium compound and at least one cerium compound, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 20% by weight, based on the total catalyst, of the K/Fe mixed oxide phases and comprises crystalline cerium dioxide having a crystallite size in the range from 10 nm to 30 nm.

The present invention further provides a process for the catalytic dehydrogenation of hydrocarbons using the catalyst of the invention.

The use of iron oxide-based catalysts in the dehydrogenation of various hydrocarbons to form the corresponding unsaturated hydrocarbons has been known for a long time in the prior art. The dehydrogenation of ethylbenzene to styrene, of isopropylbenzene to alpha-methylstyrene, of butane to butadiene or of isoamylene to isoprene, for example, are of industrial importance. The preparation of styrene by heterogeneously catalyzed dehydrogenalion of ethylbenzene in the presence of steam is a process which has been carried out industrially since the beginning of the 1930s and has become established as synthetic route to styrene. Styrene is one of the most important monomers of the plastics industry and is, for example, used for the preparation of polystyrene, acrylonitrile-butadiene-styrene polymer (ABS) and synthetic rubber.

The iron oxide-based dehydrogenation catalysts described in the prior art are generally multicomponent systems and comprise essentially iron oxide and an alkali metal compound which is, for example, used as alkali metal oxide, carbonate or hydroxide in the production of the catalyst. In addition, these catalysts generally comprise various further active components (promoters), for example oxides of the elements of transition groups 5 and 6 of the Periodic Table or of the rare earths. For example, the use of cerium compounds as promoter for such iron oxide-based dehydrogenation catalysts has been described in the prior art.

The catalytic dehydrogenation of aliphatic or alkylaromatic hydrocarbons is usually carried out industrially in the presence of steam at temperatures in the range from 500 to 700° C. In these processes, the hydrocarbon and the steam are typically mixed and passed over the iron oxide dehydrogenation catalyst at elevated temperatures.

As a result of the formation of carbonaceous material, the active sites of the dehydrogenation catalyst typically become blocked during the course of the dehydrogenation process and gradual deactivation of the catalyst occurs. To decrease this deactivation, steam is generally added to the hydrocarbon. The steam enables the carbonaceous material formed on the catalyst surface to be gasified in-situ, as a result of which the active catalyst surface can be regenerated. In addition, the steam typically also has the following functions: provision of the heat of reaction necessary for the endothermic dehydrogenation reaction, shifting of the equilibrium to the product side by reduction of the partial pressures of the starting materials, maintenance of the oxidation state of the iron in the presence of the reducing action of hydrogen and hydrocarbon.

Numerous dehydrogenation catalysts based on iron oxide have been described in the prior art.

The scientific publication by Hirano et al. (Appl. Catal. 28, 1986, p. 119-130) examines the use of cerium as promoter in an iron oxide-potassium oxide catalyst. The publication states that the addition of 5% by weight of cerium dioxide to an iron oxide-potassium oxide catalyst decreases the activation energy in the conversion of ethylbenzene into styrene and increases the reaction rate.

The document U.S. Pat. No. 4,460,706 describes dehydrogenation catalysts comprising from 40 to 87.5% by weight of $Fe_2O_3$, 11 to 50% by weight of cerium oxide (calculated as $Ce_2O_3$) and from 1.5 to 40% by weight of $K_2O$. U.S. Pat. No. 4,460,706 describes experimental examples in which catalysts having a content of 16.7% by weight of $Ce_2O_3$ are produced under various calcination conditions. A calcination time of 3 hours and a preferred temperature range for the calcination of from 900 to 1100° C. are described. U.S. Pat. No. 4,460,706 gives no information about the crystalline phase composition of the catalysts.

The document U.S. Pat. No. 6,551,958 discloses dehydrogenation catalysts comprising from 50 to 90% by weight of $Fe_2O_3$, from 1 to 40% by weight of $K_2O$, from 5 to 20% by weight of $Ce_2O_3$, from 0.1 to 10% by weight of MgO and from 1 to 10% by weight of CaO. The catalyst of U.S. Pat. No. 6,551,958 can comprise a plurality of mixed oxides of the formula $K_2O.(Fe_2O_3)_n$, where n is a natural number in the range from 1 to 11. It is stated that the formation of the KIFe mixed oxides requires calcination temperatures above 750° C. Such catalysts are produced using alpha-$Fe_2O_3$ having a specific particle size. U.S. Pat. No. 6,551,958 describes a preferred temperature range for the calcination of from 800 to 900° C. The higher activity of the catalysts of the invention is said to be related to the content of potassium-iron mixed oxide in the catalyst. U.S. Pat. No. 6,551,958 neither gives quantitative information on the proportion of the K/Fe mixed oxides in the finished catalyst nor gives an indication of the presence of cerium dioxide crystallites having a defined size.

The document EP 0 894 528 describes dehydrogenation catalysts comprising iron oxide, potassium oxide, magnesium and/or calcium oxides, cerium oxides, tungsten and/or molybdenum oxides and potassium ferrate. A two-stage process for producing the iron oxide-based dehydrogenation catalysts is described, in which a very high proportion of potassium ferrates which have the formula $K_2O.nFe_2O_3$ and are present in the form of crystallites smaller than 2 μm is said to be produced. In a first stage, a hydrated iron oxide is impregnated with an aqueous solution of cerium nitrate and kneaded with aqueous potassium hydroxide solution to form a paste, dried and calcined at from 600 to 900° C. for from 1 to 6 hours. In the second stage, the calcined intermediate is mixed with further promoters such as molybdenum, magnesium and calcium compounds, processed to form pellets and subjected to final calcination at from 600 to 900° C. for from 1 to 6 hours. In the experimental examples, the two calcination stages are carried out at 850° C. for 2 hours and at 650° C. for 4 hours. EP-A 0 894 528 neither gives quantitative information on the proportion of potassium ferrate crystallites in the finished catalyst nor gives an indication of the presence of cerium dioxide crystallites having a defined size.

The document EP-A 1 027 928 describes catalysts for the dehydrogenation of ethylbenzene to styrene which comprise a specific iron oxide obtained by spray roasting of an iron salt solution. The experimental examples describe catalysts which comprise various iron oxides and further metal components and have been calcined at 300° C. for 2 hours and at 875° C. for 1 hour. Cerium dioxide crystallite sizes of from 23 to 25 nm are reported. EP-A 1 027 928 gives no information on the use or on the presence of a potassium iron mixed oxide phase in the finished catalyst.

There is a need for further-improved dehydrogenation catalysts for the dehydrogenation of hydrocarbons, in particular for the dehydrogenation of ethylbenzene, which have an improved catalyst activity combined with improved or equal stability and operating life. It is an object of the present invention to provide an improved dehydrogenation catalyst based on iron oxide, which, in particular, has an improved catalyst activity, in particular gives an increased yield. The catalyst should likewise have a satisfactory mechanical stability and resistance to boiling water.

A further object of the present invention is to provide processes for producing the improved dehydrogenation catalysts, which processes are simple, inexpensive and reliable to carry out; in particular, no complicated process steps such as a sol-gel process and/or high calcination temperatures should be necessary in the production of the catalyst.

It has now surprisingly been found that a further improvement in the catalytic properties can be achieved by targeted optimization of the crystalline structure of the dehydrogenation catalysts. It has been found that optimized dehydrogenation yields, in particular styrene yields, can be obtained when the catalysts have a high content of K/Fe mixed oxide phases of at least 20% by weight and at the same time have cerium dioxide crystallites having a small crystallite size in the range from 10 to 30 nm. It was able to be shown that a combination of the two structural features is necessary to ensure high catalyst activities combined with good mechanical and chemical stability.

It has also been found that the crystalline structure of the catalyst which has been optimized according to the invention can be achieved, for example, by targeted setting of the calcination conditions, e.g. calcination temperature and time.

The invention provides a dehydrogenation catalyst comprising at least one iron compound, at least one potassium compound and at least one cerium compound, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 20% by weight, preferably at least 30% by weight, in particular at least 40% by weight, particularly preferably at least 60% by weight, based on the total catalyst, of the K/Fe mixed oxide phases and comprises crystalline cerium dioxide having a crystallite size in the range from 10 nm to 30 nm, preferably from 12 nm to 25 nm, preferably from 12 nm to 22 nm, particularly preferably from 14 nm to 24 nm, particularly preferably from 14 nm to 22 nm, very particularly preferably from 16 nm to 19 nm.

A BRIEF DESCRIPTION OF THE FIGURES

Figure 1:
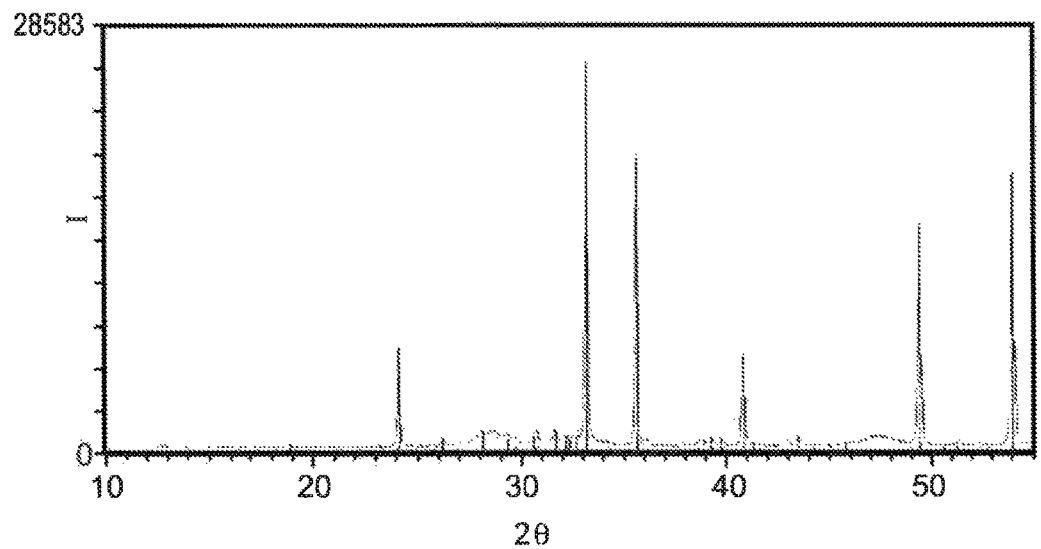
FIG. 1 shows the X-ray diffraction pattern of the catalyst V1 as per example 1 (comparative example). The X-ray diffraction pattern shows the intensity I (Lin (counts)) on the y axis and the 2 Θ (2theta) scale on the x axis.

The invention provides a dehydrogenation catalyst comprising at least one iron compound, at least one potassium compound and at least one cerium compound, wherein the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34, where the catalyst comprises at least 20% by weight, preferably at least 30% by weight, in particular at least 40% by weight, particularly preferably at least 60% by weight, based on the total catalyst, of the one or more K/Fe mixed oxide phases and comprises crystalline cerium dioxide having a crystallite size in the range from 10 nm to 30 nm, preferably from 12 nm to 25 nm, preferably from 12 nm to 22 nm, particularly preferably from 14 nm to 24 nm, particularly preferably from 14 nm to 22 nm, very particularly preferably from 16 nm to 19 nm.

Unless indicated otherwise, all the following figures in % by weight are based on the total dehydrogenation catalyst and are in each case calculated on the basis of the metal oxide in the highest oxidation state. For the purposes of the present invention, ppm means milligram per kilogram (mg/kg).

The catalysts of the invention display an improved activity compared to the catalysts described in the prior art.

For the purposes of the present invention, dehydrogenation catalyst comprising at least one iron compound, at least one potassium compound, at least one cerium compound and optionally further metal compounds means that the respective metals can be determined in the optionally indicated amounts in the catalyst. Mixed phases (e.g. oxide mixed phases) and/or isolated phases of the metal compounds described below can typically be present in the catalyst. It is additionally possible for one or more of the component(s) described below to be partly or entirely comprised in a different raw material used in catalyst production.

According to the invention, the dehydrogenation catalyst comprises at least one iron compound or at least one iron compound is used in the production of the dehydrogenation catalyst. The at least one iron compound is preferably selected from among natural or synthetic iron oxides and/or iron oxide hydroxides. In particular, the at least one iron compound is selected from the group consisting of $\alpha$-$Fe_2O_3$ (hematite), $\gamma$-$Fe_2O_3$, iron oxide hydroxide (e.g. $\alpha$-FeOOH, goethite) and $Fe_3O_4$ (magnetite). As synthetic iron oxides, it is possible to use, for example, iron oxides which have been produced by thermal decomposition of iron salt solutions.

Preference is given to using an iron oxide, in particular $Fe_2O_3$, preferably $\alpha$-$Fe_2O_3$ (hematite), as iron compound. Preference is also given to the use of $\alpha$-$Fe_2O_3$ (hematite) in combination with goethite (FeOOH) and/or magnetite ($Fe_3O_4$) as iron compound. The proportion of goethite (FeOOH) and/or magnetite ($Fe_3O_4$) is then typically from 0 to 30% by weight, based on the total amount of the iron compounds.

The specific surface area of the iron compound (e.g. determined by means of the BET method) is typically in the range from 1 to 50 $m^2/g$, preferably from 1 to 20 $m^2/g$.

The at least one iron compound is typically comprised in an amount in the range from 50 to 90% by weight, preferably from 60 to 80% by weight, particularly preferably from 65 to 75% by weight, calculated as $Fe_2O_3$, in the dehydrogenation catalyst (based on the total weight of the dehydrogenation catalyst).

According to the invention, the catalyst comprises at least one potassium compound or at least one potassium compound is used in the production of the dehydrogenation catalyst. The at least one potassium compound is preferably selected from among potassium oxide, potassium carbonate, potassium hydroxide, potassium hydrogencarbonate, potassium oxalate and K/Fe mixed oxides, in particular selected from among potassium oxide, potassium carbonate, potassium hydroxide and potassium hydrogencarbonate. The at least one potassium compound is in particular a potassium oxide ($K_2O$) or a mixed oxide. It is also possible to use another potassium compound which can be decomposed by heat. In the catalyst, the at least one potassium compound can typically be present as oxide mixed phase with the metals present in the catalyst.

The at least one potassium compound is typically comprised in an amount in the range from 1 to 30% by weight, preferably from 5 to 25% by weight, in particular from 10 to 15% by weight, based on the total weight of the dehydrogenation catalyst and calculated as $K_2O$, in the dehydrogenation catalyst.

The potassium is preferably present in the form of one or more of the K/Fe mixed oxide phases described below, in the form of mixed oxides with other catalyst components, in particular with other promoters, for example potassium molybdate, potassium tungstate, potassium vanadate, potassium manganate, and/or in the form of potassium phases, for example potassium oxide, in the finished catalyst.

According to the invention, the at least one iron compound and the at least one potassium compound are at least partly present in the form of one or more K/Fe mixed oxide phases of the general formula $K_xFe_yO_z$, where x is from 1 to 17; y is from 1 to 22 and z is from 2 to 34. These K/Fe mixed oxides or K/Fe mixed oxide phases are often referred to as potassium ferrites or potassium ferrite phases or as potassium ferrates or potassium ferrate phases.

For the purposes of the present invention, K/Fe mixed oxide phases are potassium-iron mixed oxides of the formula $K_2O \cdot nFe_2O_3$, where n is from 0.1 to 11. The potassium-iron mixed oxides can also be described by the formula $K_aFe_bO_c$, where a, b and c are natural numbers and a=1-17, b=1-22 and c=2-34. The K/Fe mixed oxide phases can be, in particular, at least one compound selected from the group consisting of $KFeO_2$, $K_2Fe_2O_4$ ($K_2O \cdot Fe_2O_3$) (where n=1); $K_2Fe_8O_{13}$ ($K_2O \cdot 4Fe_2O_3$) (where n=4); $K_2Fe_{10}O_{16}$ ($K_2O \cdot 5Fe_2O_3$) (where n=5), $K_2Fe_{22}O_{34}$ ($K_2O \cdot 11Fe_2O_3$) (where n=11), $K_6Fe_2O_5$, $K_6Fe_2O_6$, $K_9(FeO_4)_2$ (space group C2/c) and $K_{17}Fe_5O_{16}$ (space group Cm). The K/Fe mixed oxide phase is preferably at least one compound selected from the group consisting of $K_2Fe_2O_4$ ($K_2O \cdot Fe_2O_3$) (where n=1); $K_2Fe_8O_{13}$ ($K_2O \cdot 4Fe_2O_3$) (where n=4); $K_2Fe_{10}O_{16}$ ($K_2O \cdot 5Fe_2O_3$) (where n=5) and $K_2Fe_{22}O_{34}$ ($K_2O \cdot 11Fe_2O_3$) (where n=11).

The above-described K/Fe mixed oxides and mixtures thereof can be described by the general formula $K_xFe_yO_z$, where x is from 1 to 17, y is from 1 to 22 and z is from 2 to 34.

K/Fe mixed oxide phases can be formed by reaction of an iron compound, i.e. iron oxide, iron hydroxide, iron oxyhydroxide or other iron salts, and a potassium compound, e.g. potassium oxide, potassium hydroxide or other potassium salts, at elevated temperatures. The crystalline composition of the catalyst can be determined qualitatively and quantitatively by X-ray crystallography.

According to the invention, the dehydrogenation catalyst comprises at least 20% by weight, preferably at least 30% by weight, particularly preferably at least 40% by weight, in particular at least 60% by weight, based on the total catalyst, of the above-described one or more K/Fe mixed oxide phases. The catalyst preferably comprises from 20 to 98% by weight, preferably from 30 to 90% by weight, in particular from 60 to 85% by weight, based on the total catalyst, of the one or more K/Fe mixed oxide phases.

Preference is given to dehydrogenation catalysts in which the major part of the iron used in production of the catalyst is present in the form of one or more K/Fe mixed oxide phases of the general formula $K_xFe_yO_z$, as described above. It is possible for some of the iron to be present in the form of other iron oxides, for example in the form of iron oxide phases such as FeOOH, $Fe_2O_3$, in particular $\alpha$-$Fe_2O_3$ (hematite), and $Fe_3O_4$ (magnetite). A proportion of the iron used can preferably be present as hematite ($\alpha$-$Fe_2O_3$) in the finished dehydrogenation catalyst.

In particular, at least 50% by weight, preferably at least 60% by weight, in particular preferably at least 80% by weight, of the iron, based on the total amount of the iron used, calculated as $Fe_2O_3$, is present in the form of one or more of the above-described K/Fe mixed oxide phases of the general formula $K_xFe_yO_z$. In particular, from 0 to 50% by weight, preferably from 0 to 40% by weight, in particular preferably from 0 to 20% by weight, of the iron used, calculated as $Fe_2O_3$, can be present in the form of a hematite phase ($\alpha$(alpha)-$Fe_2O_3$).

According to the invention, the dehydrogenation catalyst comprises at least one cerium compound or at least one cerium compound is used in the production of the dehydrogenation catalyst. The at least one cerium compound is preferably selected from among cerium oxides, cerium hydroxides, cerium carbonates, water-containing cerium carbonates and cerium oxalates. Mixtures of the cerium compounds mentioned can preferably be used. The at least one cerium compound is preferably selected from among cerium(IV) oxide ($CeO_2$), cerium(III) oxide ($Ce_2O_3$), cerium(III) oxalate and cerium(III) carbonate, preferably from among cerium(IV) oxide ($CeO_2$) and cerium(III) carbonate. The at least one cerium compound is typically converted into cerium dioxide, in particular crystalline cerium dioxide, during production of the catalyst.

The dehydrogenation catalyst preferably comprises from 2 to 25% by weight, preferably from 5 to 20% by weight, preferably from 7 to 20% by weight, in particular preferably from 10 to 20% by weight, of at least one cerium compound, calculated as $CeO_2$.

According to the invention, the catalyst comprises crystalline cerium dioxide which has a crystallite size in the range from 10 nm to 30 nm, preferably from 12 nm to 25 nm, preferably from 12 nm to 22 nm, particularly preferably from 14 nm to 24 nm, particularly preferably from 14 nm to 22 nm, very particularly preferably from 16 nm to 19 nm.

In particular, at least 50% by weight, preferably at least 60% by weight, preferably at least 80% by weight, in particular preferably at least 90% by weight, of the cerium, based on the total amount of the cerium used, calculated as $CeO_2$, is present in the form of the above-described crystalline cerium dioxide having the crystallite size described.

For the purposes of the present invention, crystallit is a single crystal (also referred to as single crystal grain) in a polycrystalline material such as the catalyst material, with these single crystals being able to be embedded in an amorphous, partially crystalline or crystalline matrix and/or being able to be present side by side with single crystals of a different type. In particular, crystallites in a polycrystalline material are separated from one another and/or from the matrix by their grain boundaries. The crystallites form, possibly together with the surrounding matrix, a polycrystalline material, with various types of crystallites being able to be present in the polycrystalline material.

For the purposes of the present invention, the crystallite size is the average size of the crystallites or the crystallite grains which are present in the catalyst as polycrystalline material. In particular, the term crystallite size refers to the average size of the crystallites in the catalyst, which can be determined by means X-ray structure analysis (X-ray diffraction XRD) and evaluation of the peak width by means of the Scherrer equation. The crystallite size determined in this way gives information on the dimensions of the crystalline grains in the catalyst material, with agglomerates of the grains or crystallites not being measured.

Cerium is predominantly comprised in the form of cerium dioxide, in particular as crystalline cerium dioxide, in particular as crystalline cerium dioxide in the form of cerianite, in the catalyst of the invention. The cerium can optionally also be at least partly present as mixed compounds, in particular as mixed oxide, with other catalyst components in the catalyst.

The catalyst of the invention comprises cerium dioxide crystallites which consist essentially of crystalline cerium dioxide, preferably of crystalline cerium dioxide in the form of cerianite, and are present as finely disperse crystallite grains having an average diameter of from 10 nm to 30 nm, preferably from 12 nm to 25 nm, preferably from 12 nm to 22 nm, particularly preferably from 14 nm to 24 nm, particularly preferably from 14 nm to 22 nm, very particularly preferably from 16 nm to 19 nm.

The dehydrogenation catalyst preferably comprises at least one alkaline earth metal compound as further component, or at least one alkaline earth metal component is used in the production of the dehydrogenation catalyst. In particular, the dehydrogenation catalyst can comprise from 0.1 to 20% by weight, in particular from 0.1 to 10% by weight, preferably from 1 to 5% by weight, of at least one alkaline earth metal compound, calculated as oxide, as further component.

In a preferred embodiment, the dehydrogenation catalyst comprises at least one magnesium compound as further component. The dehydrogenation catalyst preferably comprises from 0.1 to 10% by weight, preferably from 1 to 5% by weight, of at least one magnesium compound, calculated as MgO, as further component. In particular, the at least one magnesium compound is selected from among magnesium oxide, magnesium carbonate and magnesium hydroxide. The at least one magnesium compound is preferably magnesium oxide (MgO) and/or magnesium carbonate ($MgCO_3$). Preference is given to using magnesium oxide (MgO) and/or magnesium carbonate ($MgCO_3$) as further component in the production of the catalyst.

In a preferred embodiment, the dehydrogenation catalyst comprises at least one calcium compound as further component. The dehydrogenation catalyst preferably comprises from 0.1 to 10% by weight, preferably from 1 to 5% by weight, of at least one calcium compound, calculated as CaO, as further component. In particular, the at least one calcium compound is selected from among calcium oxide, calcium carbonate and calcium hydroxide. The at least one calcium compound is preferably calcium oxide (CaO). Preference is given to using calcium oxide (CaO) and/or calcium hydroxide ($Ca(OH)_2$) as further component in the production of the catalyst.

In a preferred embodiment, the dehydrogenation catalyst comprises at least one magnesium compound and at least one calcium compound. In particular, the dehydrogenation catalyst comprises from 0.1 to 10% by weight, preferably from 1 to 5% by weight, of at least one magnesium compound, calculated as MgO, and also from 0.1 to 10% by weight, preferably from 1 to 5% by weight, of at least one calcium compound, calculated as CaO.

A preferred embodiment of the present invention provides a dehydrogenation catalyst comprising from 50 to 90% by weight, preferably from 60 to 80% by weight, of at least one iron compound, calculated as $Fe_2O_3$;

from 1 to 30% by weight, preferably from 5 to 25% by weight, of at least one potassium compound, calculated as $K_2O$;

from 2 to 25% by weight, preferably from 7 to 20% by weight, preferably from 10 to 20% by weight, of at least one cerium compound, calculated as $CeO_2$;

from 0.1 to 10% by weight, preferably from 0.1 to 5% by weight, of at least one magnesium compound, calculated as MgO;

from 0.1 to 10% by weight, preferably from 0.1 to 5% by weight, of at least one calcium compound, calculated as CaO; and from 0 to 30% by weight, preferably from 0.0001 to 10% by weight, of at least one further component.

In a preferred embodiment, the abovementioned components add up to 100% by weight.

The further components can be comprised (or be added) in amounts of from 0 to 30% by weight, preferably from 0 to 20% by weight, preferably from 0.0001 to 10% by weight, in particular from 0.001 to 5% by weight, in particular from 0.5 to 5% by weight.

The dehydrogenation catalyst can typically comprise one or more of the usual compounds for increasing the activity and/or selectivity as at least one further component, in particular as promoter or dopant. For example, at least one compound selected from compounds encompassing a metal selected from the group consisting of Mn, Ti, Cr, Co, Ni, Cu, Zn, Al, Ga, Ge, Zr, Nb, Ru, Rh, Pd, Ag, Cd, In, Sn, Sb, La, Hf, Ta, Re, Ir, Pt, Au, Pb and Bi can be comprised as further component, or at least one such compound is used in the production of the dehydrogenation catalyst. It is also possible for one or more of the abovementioned components to be comprised partly or entirely in a different raw material used in the production of the catalyst, for example in the iron oxide. The customary components mentioned, in particular promoters or dopants, can typically be comprised in amounts of from 0 to 10% by weight, preferably from 0.0001 to 5% by weight, preferably from 0.001 to 2% by weight, in each case calculated as oxide in the highest oxidation state, based on the total catalyst.

The dehydrogenation catalyst can preferably comprise at least one compound selected from compounds encompassing a metal selected from the group consisting of manganese (Mn), molybdenum (Mo), titanium (Ti), vanadium (V) and tungsten (W), preferably selected from the group consisting of molybdenum (Mo), titanium (Ti), vanadium (V) and tungsten (W), as further component; or at least one such compound is used in the production of the dehydrogenation catalyst. The further component can in particular be selected from among oxygen compounds, for example oxides, oxide hydrates, oxo compounds, of manganese (Mn), molybdenum (Mo), titanium (Ti), vanadium (V) and tungsten (W). In particular, the at least one compound selected from compounds encompassing a metal selected from the group consisting of manganese (Mn), molybdenum (Mo), titanium (Ti), vanadium (V) and tungsten (W) is a compound which decomposes under the action of heat in the production of the dehydrogenation catalyst.

The dehydrogenation catalyst preferably comprises from 0.0001 to 10% by weight, preferably from 0.001 to 5% by weight, particularly preferably from 0.5 to 5% by weight, of at least one compound selected from the group consisting of manganese (Mn), molybdenum (Mo), titanium (Ti), vanadium (V) and tungsten (W), preferably selected from the group consisting of molybdenum (Mo), titanium (Ti), vanadium (V) and tungsten (W), calculated as oxide in the highest oxidation state in each case, as further component.

The dehydrogenation catalyst preferably comprises from 0.0001 to 10% by weight, preferably from 0.001 to 5% by weight, particularly preferably from 0.5 to 5% by weight, of at least one compound selected from compounds encompassing a metal selected from the group consisting of manganese (Mn), molybdenum (Mo), titanium (Ti), vanadium (V) and tungsten (W), preferably selected from the group consisting of molybdenum (Mo), titanium (Ti), vanadium (V) and tungsten (W), calculated as oxide in the highest oxidation state in each case, as further component.

Preference is given to using at least one molybdenum compound selected from among molybdenum oxides and molybdates (e.g. ammonium molybdate, potassium molybdate) as at least one further component. The at least one molybdenum compound is preferably molybdenum oxide.

In particular, the dehydrogenation catalyst comprises from 0.1 to 10% by weight, preferably from 0.5 to 5% by weight, of at least one molybdenum compound, calculated as $MoO_3$, as further component.

In particular, the dehydrogenation catalyst comprises at least one titanium compound as further component; or at least one titanium compound can be used in the production of the dehydrogenation catalyst. The dehydrogenation catalyst can comprise from 0 to 1000 ppm, preferably from 10 to 500 ppm, preferably from 30 to 500 ppm, particularly preferably from 50 to 220 ppm, of the at least one titanium compound, calculated as $TiO_2$, based on the total catalyst.

The at least one titanium compound can in particular be selected from among titanium oxides, titanium alkoxides and titanium carboxylates. The at least one titanium compound is preferably titanium dioxide ($TiO_2$). The at least one titanium compound is preferably added as titanium dioxide ($TiO_2$) in the production of the catalyst. However, it is also possible to use other titanium compounds. It is additionally possible for the at least one titanium compound to be partly or entirely comprised in a different raw material used in catalyst production, e.g. in the iron oxide.

In particularly, the dehydrogenation catalyst comprises from 0.1 to 10% by weight, particularly preferably from 1 to 5% by weight, of at least one vanadium compound, calculated as $V_2O_5$, as further component.

In a preferred embodiment, the present invention provides a dehydrogenation catalyst as described above comprising:
from 50 to 90% by weight, preferably from 60 to 80% by weight, of at least one iron compound, calculated as $Fe_2O_3$;
from 1 to 30% by weight, preferably from 5 to 25% by weight, in particular from 10 to 20% by weight, of at least one potassium compound, calculated as $K_2O$;
from 2 to 25% by weight, preferably from 5 to 20% by weight, preferably from 7 to 20% by weight, in particular from 10 to 20% by weight, of at least one cerium compound, calculated as $CeO_2$;
from 0.1 to 10% by weight, preferably from 1 to 5% by weight, of at least one magnesium compound calculated as MgO;
from 0.1 to 10% by weight, preferably from 1 to 5% by weight, of at least one calcium compound, calculated as CaO; and
from 0.0001 to 10% by weight, preferably from 0.001 to 5% by weight, of at least one compound selected from compounds encompassing a metal selected from the group consisting of manganese (Mn), molybdenum (Mo), titanium (Ti), vanadium (V) and tungsten (W), in each case calculated as the oxide in the highest oxidation state.

In a preferred embodiment, the abovementioned components add up to 100% by weight.

In a preferred embodiment, the present invention provides a dehydrogenation catalyst as described above comprising:
from 50 to 90% by weight, preferably from 60 to 80% by weight, of at least one iron compound, calculated as $Fe_2O_3$;
from 1 to 30% by weight, preferably from 5 to 25% by weight, in particular from 10 to 20% by weight, of at least one potassium compound, calculated as $K_2O$;
from 2 to 25% by weight, preferably from 5 to 20% by weight, preferably from 7 to 20% by weight, in particular from 10 to 20% by weight, of at least one cerium compound, calculated as $CeO_2$;
from 0.1 to 10% by weight, preferably from 0.1 to 5% by weight, in particular from 1 to 4% by weight, of at least one magnesium compound, calculated as MgO;
from 0.1 to 10% by weight, preferably from 0.1 to 5% by weight, in particular from 1 to 4% by weight, of at least one calcium compound, calculated as CaO;
from 0.1 to 10% by weight, preferably from 0.1 to 5% by weight, in particular from 0.5 to 4% by weight, of at least one molybdenum compound, calculated as $MoO_3$ and
from 1 to 1000 ppm, preferably from 10 to 500 ppm, preferably from 30 to 500 ppm, in particular from 50 to 220 ppm, of at least one titanium compound, calculated as $TiO_2$.

In a preferred embodiment, the abovementioned components add up to 100% by weight.

In a preferred embodiment, the present invention provides a dehydrogenation catalyst as described above comprising:
from 50 to 90% by weight, preferably from 60 to 80% by weight, of at least one iron compound, calculated as $Fe_2O_3$;
from 1 to 30% by weight, preferably from 5 to 25% by weight, in particular from 10 to 20% by weight, of at least one potassium compound, calculated as $K_2O$;
from 2 to 25% by weight, preferably from 5 to 20% by weight, preferably from 7 to 20% by weight, in particular from 10 to 20% by weight, of at least one cerium compound, calculated as $CeO_2$;
from 0.1 to 10% by weight, preferably from 0.1 to 5% by weight, in particular from 1 to 4% by weight, of at least one magnesium compound, calculated as MgO;
from 0.1 to 10% by weight, preferably from 0.1 to 5% by weight, in particular from 1 to 4% by weight, of at least one calcium compound, calculated as CaO;
from 0.1 to 10% by weight, preferably from 0.1 to 5% by weight, in particular from 0.5 to 4% by weight, of at least one molybdenum compound, calculated as $MoO_3$;

from 0.1 to 20% by weight, preferably from 0.1 to 10% by weight, preferably from 0.2 to 5% by weight, in particular from 0.7 to 2% by weight, of at least one manganese compound, calculated as $MnO_2$; and from 1 to 1000 ppm, preferably from 10 to 500 ppm, preferably from 30 to 500 ppm, in particular from 50 to 220 ppm, of at least one titanium compound, calculated as $TiO_2$.

In a preferred embodiment, the abovementioned components add up to 100% by weight.

All figures in % by weight relate, unless indicated otherwise, to the total dehydrogenation catalyst. All figures in % by weight have, unless indicated otherwise, been calculated on the basis of the oxide of the respective metal in each case in the highest oxidation state.

In an embodiment, the above-described dehydrogenation catalyst comprises at least one further rare earth metal compound apart from cerium, in particular selected from the group consisting of lanthanum (La), praseodymium (Pr) and neodymium (Nd), as further component. The dehydrogenation catalyst preferably comprises from 1 to 1000 ppm, preferably from 10 to 500 ppm, particularly preferably from 20 to 300 ppm, of at least one further rare earth metal compound apart from cerium, calculated as oxide in the highest oxidation state in each case. In particular, the catalyst comprises from 1 to 1000 ppm, preferably from 10 to 500 ppm, particularly preferably from 20 to 300 ppm, of at least one rare earth metal compound selected from the group consisting of lanthanum, praseodymium and neodymium. The dehydrogenation catalyst can preferably comprise from 1 to 1000 ppm, preferably from 3 to 500 ppm, particularly preferably from 10 to 100 ppm, of at least one lanthanum compound, calculated as $La_2O_3$, as further component. The dehydrogenation catalyst can preferably comprise from 1 to 1000 ppm, preferably from 3 to 500 ppm, particularly preferably from 10 to 100 ppm, of at least one praseodymium compound, calculated as $PrO_2$, as further component. The dehydrogenation catalyst can preferably comprise from 1 to 1000 ppm, preferably from 3 to 500 ppm, particularly preferably from 10 to 100 ppm, of at least one neodymium compound, calculated as $Nd_2O_3$, as further component.

The above-described dehydrogenation catalyst can preferably comprise at least one compound of metals of transition groups 8 to 12 of the Periodic Table as further component. The above-described dehydrogenation catalyst preferably comprises at least one compound of metals selected from the group consisting of manganese (Mn), ruthenium (Ru), osmium (Os), cobalt (Co), nickel (Ni), palladium (Pd), platinum (Pt), copper (Cu), silver (Ag), gold (Au) and zinc (Zn); preferably selected from the group consisting of cobalt (Co), manganese (Mn), palladium (Pd), copper (Cu) and zinc (Zn); particularly preferably selected from the group consisting of manganese (Mn), copper (Cu), and zinc (Zn), as further component. The above-described dehydrogenation catalyst can comprise, in particular, from 1 to 1000 ppm, preferably from 50 to 500 ppm, particularly preferably from 50 to 200 ppm, of at least one compound of metals of transition groups 8 to 12 of the Periodic Table, in each case calculated as oxide in the highest oxidation state, as further component. In a preferred embodiment, the above-described dehydrogenation catalyst comprises from 1 to 1000 ppm, preferably from 50 to 500 ppm, particularly preferably from 50 to 200 ppm, of at least one compound of metals selected from the group consisting of manganese (Mn), copper (Cu) and zinc (Zn), in each case calculated as the oxide in the highest oxidation state. The dehydrogenation catalyst can preferably comprise from 1 to 1000 ppm, preferably from 30 to 500 ppm, particularly preferably from 30 to 200 ppm, of at least one manganese compound, calculated as $MnO_2$, as further component. The dehydrogenation catalyst can preferably comprise from 1 to 1000 ppm, preferably from 10 to 200, particularly preferably from 30 to 100 ppm, of at least one copper compound, calculated as CuO, as further component. The dehydrogenation catalyst can preferably comprise from 1 to 1000 ppm, preferably from 1 to 500 ppm, particularly preferably from 10 to 100 ppm, of at least one zinc compound, calculated as ZnO, as further component.

In addition, the dehydrogenation catalyst can comprise at least one compound of elements of main group 4 of the Periodic Table of the Elements as further component. The above-described dehydrogenation catalyst preferably comprises at least one compound selected from the group consisting of silicon (Si), germanium (Ge), tin (Sn), and lead (Pb) compounds, preferably at least one silicon compound, as further component. In particular, the dehydrogenation catalyst comprises from 1 to 1000 ppm, preferably from 5 to 500 ppm, particularly preferably from 10 to 100 ppm, of at least one compound of selected from the group consisting of silicon (Si), germanium (Ge), tin (Sn) and lead (Pb) compound, calculated as oxide in each case in the highest oxidation state. In one embodiment, the dehydrogenation catalyst described comprises from 1 to 1000 ppm, preferably from 5 to 500 ppm, particularly preferably from 10 to 100 ppm, of at least one silicon compound, calculated as $SiO_2$.

The above-described dehydrogenation catalyst can typically comprise at least one nonmetal selected from among nonmetals of main groups 5 to 7 of the Periodic Table, in particular selected from the group consisting of nitrogen, phosphorus, sulfur and chlorine, as nonmetal apart from oxygen.

The dehydrogenation catalyst of the invention can, in particular, have a specific surface area in the range from 1 to 3 $m^2/g$, in particular from 1.5 to 2.5 $m^2/g$. The specific surface area of the catalysts can, for example, be determined by means of the nitrogen adsorption method, for example as described in DIN ISO 9277.

In particular, the present invention provides a dehydrogenation catalyst as described above for the catalytic dehydrogenation of hydrocarbons in a molar steam/hydrocarbon ratio of from 1 to 20; preferably in the range from 1 to 10; in particular in the range from 1 to 9, particularly preferably from 5 to 8.5.

In a further aspect, the present invention provides a process for producing a dehydrogenation catalyst as described above, which comprises the following steps:
i) production of a catalyst premix by mixing of at least one iron compound, at least one potassium compound, at least one cerium compound and optionally further metal compounds, optionally further components and optionally at least one binder with a solvent;
ii) production of shaped catalyst bodies from the catalyst premix obtained in step i);
iii) drying of the shaped catalyst bodies and calcination of the shaped catalyst bodies, where the calcination of the shaped catalyst bodies are carried out at a temperature in the range from 600° C. to 1000° C., preferably from 700° C. to 950° C., preferably from 750° C. to 900° C., in particular from 600° C. to 850° C., and for a time of from 10 minutes to 300 minutes, preferably from 15 minutes to 240 minutes.

In the process for producing a dehydrogenation catalyst, preference is given to using the iron compounds, potassium compounds, cerium compounds and further components, in particular further metal compounds, described above in relation to the dehydrogenation catalyst, preferably in the amounts described. The above-described components can optionally be used in the production process; one or more of the components is/are optionally present partly or completely in one of the raw materials used, for example in the used iron oxide and/or cerium carbonate.

The basic procedure in the production of dehydrogenation catalysts is known to those skilled in the art. The production of the above-described dehydrogenation catalysis can be carried out, for example, as described in U.S. Pat. No. 6,551,958.

The choice of the catalyst components (starting materials, raw materials) and the choice of the production conditions, in particular the calcination conditions, can be made in such a way that catalysts according to the invention having the combination of structural features described are obtained. A production process having very few steps, in particular very few calcination steps, is particularly advantageous.

It has, for example, been found that the catalysts of the invention which have the above-described advantageous combination of structural features (proportion of K/Fe mixed oxide phases and $CeO_2$ crystallite size) can preferably be obtained by setting and controlling the temperature and also the duration or the residence time of the calcination. K/Fe mixed oxide phases of the general formula $K_xFe_yO_z$, where x is from 1 to 17; y is from 1 to 22 and z is from 2 to 34, can, for example, be formed by reaction of the at least one iron compound and the at least one potassium compound during the final calcination of the catalyst in the presence of all other constituents of the catalyst.

It has, in particular, been found that high calcination temperatures and long calcination times are necessary for the formation of K/Fe mixed oxide phases, but on the other hand high temperatures and long calcination times lead to an increase in the cerium dioxide crystallite size, which can, for example, be attributed to the cerium dioxide crystallites sintering and thus growing in size. Optimal combinations of temperature and duration of calcination in step iii), inter alia, have been found. Basically, the catalysts according to the invention can be obtained by step iii) being carried out either at lower calcination temperatures over a longer period of time or at higher calcination temperatures over a shorter period of time within the limits indicated.

To produce the catalyst premix, the components, typically in the form of solid powders, are generally mixed and then mixed with a solvent, in particular water, optionally with addition of a binder. Mixing is preferably carried out by intimate mixing, e.g. by kneading, in a stirred vessel, mix-muller, mixer, kneader or extruder, preferably in a mix-muller, kneader or mixer. In this context, a solvent is, in particular, a liquid solvent and/or dispersion medium in which the solid catalyst components are dispersed.

As solvent, use is made of, in particular, water or a mixture of water and polar solvents, e.g. alcohols, esters. As binder (also plasticizer), it is possible to use, for example, alginate, starch, carboxymethylcellulose, hydroxyethylcellulose and polyvinyl alcohol. The binders are typically used in the form of a solution in water.

Shaped catalyst bodies are then typically produced from the resulting catalyst premix and are subsequently dried and calcined.

The production of shaped catalyst bodies from the catalyst premix is typically carried out by extrusion or pressing (tableting). Examples of shaped catalyst bodies are cylinders (pellets), rings, star bodies and honeycomb bodies. The production of shaped catalyst bodies from the catalyst premix obtained in step i) is preferably carried out by means of extrusion.

After shaping, the moist shaped bodies are typically dried at temperatures of from 50° C. to 500° C., preferably from 80 to 350° C. Drying can, for example, take place in a drying oven (e.g. on metal trays), in a drying drum and/or on belt dryers.

The shaped bodies are then generally calcined. Calcination can be carried out in muffle furnaces, belt calciners, rotary tube furnaces, etc. The catalyst extrudants are preferably calcined in a rotary tube furnace.

The shaped catalyst bodies are preferably calcined at temperatures in the range from 600° C. to 1000° C., preferably from 700° C. to 950° C., preferably from 750° C. to 900° C., in particular from 600° C. to 850° C., in step iii). Calcination can, for example, be carried out in a rotary tube furnace.

In a preferred embodiment, the invention provides a process for producing a dehydrogenation catalyst as described above, wherein the calcination of the shaped catalyst bodies in step iii) are carried out at temperatures in the range from 600° C. to 850° C., preferably from 750° C. to 850° C., particularly preferably from 775° C. to 825° C., and for a time of from 10 minutes to 300 minutes, preferably from 30 minutes to 180 minutes, particularly preferably from 30 minutes to 90 minutes, very particularly preferably from 30 minutes to 60 minutes, or at temperatures in the range from 800° C. to 1000° C., preferably from 850° C. to 1000° C., preferably from 850° C. to 900° C., and over a time of from 10 minutes to 60 minutes, preferably from 10 minutes to 50 minutes, preferably from 10 minutes to 30 minutes.

The calcination in step iii) can preferably be carried out at temperatures of from 700° C. to 850° C., preferably from 700° C. to 825° C., particularly preferably from 750° C. to 800° C., and for a calcination time of from 15 minutes to 90 minutes, preferably from 30 minutes to 60 minutes. The process can, for example, be carried out as a stationary process, for example in a muffle furnace.

The calcination in step iii) can preferably be carried out at temperatures of from 800° C. to 950° C., preferably from 850° C. to 900° C., and for a calcination time of from 10 minutes to 30 minutes, preferably from 10 minutes to 20 minutes. The process can, for example, be carried out as a continuous process, for example in a continuous rotary tube furnace. In a continuous process, the residence time typically corresponds to the above-described calcination time.

As compounds and further components, it is possible to use compounds in the form in which they are present in the finished catalyst or compounds which are converted during the production process into compounds in the form in which they are present in the finished catalyst. Preference is given to using the compounds described in connection with the dehydrogenation catalyst of the invention.

In particular, the invention provides a process for producing a dehydrogenation catalyst as described, wherein an iron compound comprising at least 50% by weight, preferably at least 80% by weight, based on the total iron compound, of iron(III) oxide ($Fe_2O_3$) is used. Hematite ($Fe_2O_3$) is predominantly used as iron component. Part of the iron can be used as goethite (FeOOH) or magnetite ($Fe_3O_4$), with this proportion being able to be from 0 to 30%. In particular, the invention provides a process for producing a dehydrogenation catalyst as described, wherein a potassium oxide, potassium hydroxide, potassium carbonate and/or potassium hydrogencarbonate is used as potassium compound. As cerium compound, preference is given to using cerium oxides, in particular cerium dioxide, cerium carbonates, cerium hydroxides and/or cerium hydrogencarbonates. As magnesium compound, preference is given to using magnesium oxide, magnesium carbonate and/or magnesium hydroxide. As calcium compound, preference is given to using calcium oxide, calcium carbonate and/or calcium hydroxide. As titanium compound, preference is given to using titanium oxides, in particular $TiO_2$, titanium alkoxides and/or titanium carboxylates. As molybdenum compound, preference is given to using molybdenum oxides, in particular $MoO_3$. As vanadium compound, preference is given to using vanadium oxides.

In a further aspect, the present invention provides a process for the catalytic dehydrogenation of a hydrocarbon, wherein a mixture of steam and at least one hydrocarbon is brought into contact with a dehydrogenation catalyst as described above.

The preferred embodiments described above in connection with the dehydrogenation catalyst of the invention and the process for producing it apply analogously to the process of the invention for the catalytic dehydrogenation of a hydrocarbon.

The process for the catalytic dehydrogenation of a hydrocarbon using the dehydrogenation catalyst of the invention gives an improved yield, for example an improved styrene yield, compared to known processes or dehydrogenation catalysts.

The present invention preferably provides a process for the catalytic dehydrogenation of a hydrocarbon, wherein a mixture of steam and at least one hydrocarbon having a molar steam/hydrocarbon ratio in the range from 1 to 20; preferably from 1 to 10; in particular form 1 to 9; particularly preferably from 5 to 8.5; is used. In particular, the invention provides a process for the catalytic dehydrogenation of ethylbenzene to styrene, wherein a mixture of steam and ethylbenzene having a steam/hydrocarbon weight ratio in the range from 0.17 to 3.4; preferably from 0.17 to 1.7; in particular from 0.17 to 1.5; particularly preferably from 0.9 to 1.45; is used. The catalytic dehydrogenation according to the invention of a hydrocarbon can particularly preferably be carried out using an average steam/hydrocarbon weight ratio in the range from 0.9 to 1.45 (kg/kg).

In the process of the invention for catalytic dehydrogenation, yields of from 40 to 80%, preferably from 50 to 75%, particularly preferably from 60 to 70%, based on the hydrocarbon used, are typically achieved per pass through the reactor. In particular, styrene yields of 40 to 80%, preferably from 50 to 75%, particularly preferably from 60 to 70%, based on the ethylbenzene used, are achieved per pass through the reactor in the catalytic dehydrogenation of ethylbenzene. The yields indicated are based on mol %.

The process for the catalytic dehydrogenation of a hydrocarbon is typically carried out at temperatures of from 500 to 650° C. and pressures of from 0.2 to 2 bar absolute.

The process described can be the dehydrogenation of alkylaromatic or aliphatic hydrocarbons; it is preferably the dehydrogenation of alkylaromatic hydrocarbons, particularly preferably the dehydrogenation of ethylbenzene to styrene. The process of the invention for the dehydrogenation of a hydrocarbon can be, for example, the dehydrogenation of ethylbenzene to styrene, of isopropylbenzene to alpha-methylstyrene, of butene to butadiene or of isoamylene to isoprene. The hydrocarbon is preferably ethylbenzene.

Furthermore, the present invention provides for the use of a dehydrogenation catalyst as described above for the catalytic dehydrogenation of a hydrocarbon, in particular an alkylaromatic or aliphatic hydrocarbon, preferably an alkylaromatic hydrocarbon, particularly preferably ethylbenzene. The invention preferably provides for the use of a dehydrogenation catalyst as described above for the catalytic dehydrogenation of a hydrocarbon at a molar steam/hydrocarbon ratio in the range from 1 to 20; preferably in the range from 1 to 10; in particular in the range from 1 to 9; particularly preferably in the range from 5 to 8.5.

The figures are explained below:

FIG. 1 shows the X-ray diffraction pattern of the catalyst V1 as per example 1 (comparative example). The X-ray diffraction pattern shows the intensity I ($L_{in}$ (counts)) on the y axis and the 2 Θ (2theta) scale on the x axis.

Figure 2:
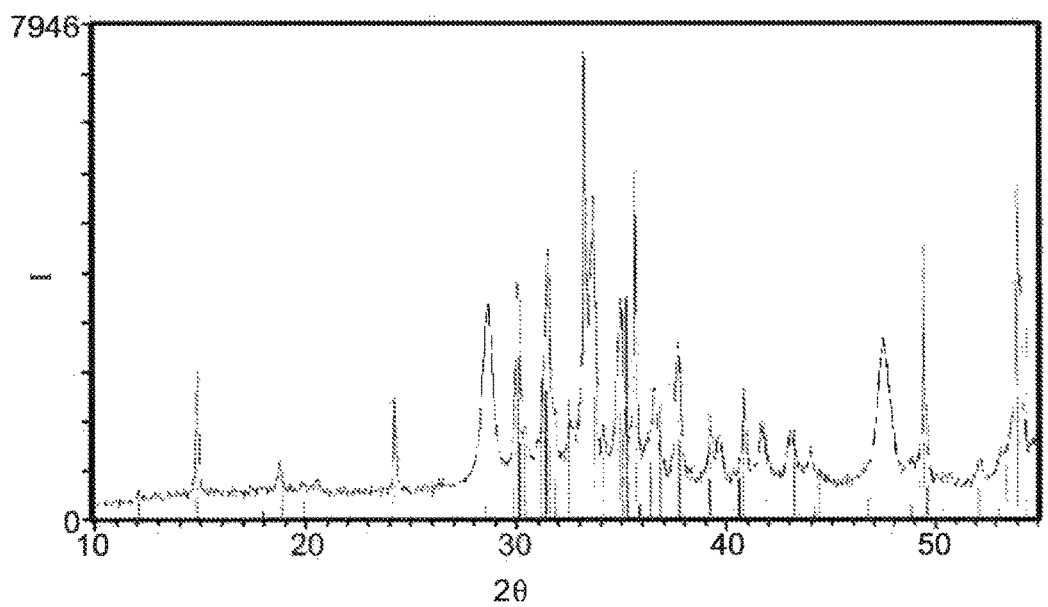
FIG. 2 shows the X-ray diffraction pattern of the catalyst K5 as per example 5 (example according to the invention). The X-ray diffraction pattern shows the intensity I (Lin (counts)) on the y axis and the 2 Θ (2theta) scale on the x axis.

FIG. 2 shows the X-ray diffraction pattern of the catalyst K5 as per example 5 (example according to the invention). The X-ray diffraction pattern shows the intensity I ($L_{in}$ (counts)) on they axis and the 2 Θ (2theta) scale on the x axis.

The present invention is illustrated by the following examples.

EXAMPLES

Example 1 (Comparative Example)

Components used were iron oxide (alpha-$Fe_2O_3$, hematite), potassium carbonate ($K_2CO_3$), cerium carbonate ($Ce_2CO_3$), magnesium oxide (MgO), molybdenum oxide ($MoO_3$), calcium hydroxide ($Ca(OH)_2$), manganese dioxide ($MnO_2$) and titanium dioxide ($TiO_2$).

The abovementioned pulverant components were firstly mixed dry and then kneaded with addition of water and starch solution. The catalyst composition was extruded, giving pellets having a diameter of 3 mm. The shaped catalyst bodies (pellets) were dried at 120° C. for 1 hour, then at 350° C. for 1 hour and calcined at 500° C. for 1 hour in air in a muffle furnace.

A catalyst K1 having the following nominal oxide composition was obtained:
71.1% by weight of $Fe_2O_3$,
13.6% by weight of $K_2O$,
7.4% by weight of $CeO_2$,
2.2% by weight of MgO,
2.0% by weight of CaO,
2.1% by weight of $MoO_3$,
1.6% by weight of $MnO_2$ and
70 ppm of $TiO_2$.

Example 2 (Comparative Example)

A catalyst was produced as described in example 1, with the only difference being that the final calcination took place at 870° C. for 1 hour.

The catalyst K2 having the abovementioned nominal composition was obtained.

Example 3 (Comparative Example)

A catalyst was produced as described in example 1, with the only difference being that the final calcination took place at 1000° C. for 1 hour.

The catalyst K3 having the abovementioned nominal composition was obtained.

Examples 4 to 8 (Examples According to the Invention)

A catalyst was produced as described in example 1, with the only difference being that the final calcination was carried out at various temperatures in the range from 775° C. to 825° C. and over various periods of time in the range from 30 minutes to 60 minutes. The calcination was, as in comparative example 1, carried out in a stationary manner in an air atmosphere in a muffle furnace.

The catalysts K4 to K8 having the abovementioned nominal composition were obtained.

The calcination conditions are summarized in table 1 below.

Example 9: Characterization of the Catalysts a) The specific surface areas of the catalysts K1 to K8 were determined by means of the nitrogen adsorption method in accordance with DIN ISO 9277.

b) The crystallographic phase compositions, e.g. content of K/Fe mixed oxide phases and cerium dioxide crystallite size, were determined by X-ray diffraction measurements using the following method:

The shaped catalyst bodies were milled to a fine powder in a mill. The samples were then introduced into a standard sample holder (from Bruker AXS GmbH) and struck smooth using a glass plate. The samples were measured in a D8 Advance Diffractometer (from Bruker AXS GmbH) using a variable orifice plate (V20—irradiated sample length of 20 mm) and an energy-dispersive point detector (Sol-X, from Bruker AXS GmbH) in the angle range from 10° to 55° 2θ (2 theta) using a step width of 0.02° 2θ (2 theta). The data were evaluated using the software TOPAS 4.2 (from Bruker AXS GmbH). The phase composition of the catalysts typically comprised variable proportions of various crystallographic phases, e.g. cerianite ($CeO_2$), hematite ($Fe_2O_3$), magnetite ($Fe_3O_4$), $K_2CO_3 \cdot 1.5H_2O$, $K_4H_2(CO_3)_3 \cdot 1.5H_2O$, $KFe_{11}O_{17}$, $K_2Fe_{10}O_{16}$, $K_6Fe_2O_5$, $K_6Fe_2O_6$, $K_9(FeO_4)_2$ (space group C2/c) and $K_{17}Fe_5O_{16}$ (space group Cm), $K_2Fe_2O_4$, $KFeO_2$ and possibly other oxidic phases which are dependent on the further metal compounds present. In all phases, the lattice parameters, crystallite size and scale were refined and in the case of $KFe_{11}O_{17}$ additionally the Gaussian component of the lattice strain and a March-Dollase preferential orientation in the (001) direction. The background was fitted using a third order polynominal, and the sample height error was refined. Intensity corrections for the Lorentz polarization were taken into account. The crystallite size is the value calculated by the TOPAS "Lvol FWHM" software.

TABLE 1

Calcination conditions and properties of the catalysts K1 to K8

| Catalyst | Calcination temperature and time | Specific surface area $m^2/g$ | Average $CeO_2$ crystallite size nm | K/Fe Mixed oxide phases % by weight | Hematite % by weight |
|---|---|---|---|---|---|
| K1 | 500° C./60 min | 1.6 | 6 | 16 | 69 |
| K2 | 870° C./60 min | 1.2 | 38 | 83 | <1 |
| K3 | 1000° C./60 min | 1.2 | 112 | 84 | <1 |
| K4 | 775° C./30 min | 1.6 | 14 | 40 | 44 |
| K5 | 775° C./60 min | 1.8 | 16 | 68 | 17 |
| K6 | 800° C./30 min | 2.1 | 16 | 61 | 25 |
| K7 | 800° C./60 min | 1.8 | 19 | 80 | 5 |
| K8 | 825° C./60 min | 1.6 | 24 | 81 | 4 |

Examples 10 and 11: Catalyst Production with Continuous Calcination

Catalysts were produced as described in comparative example 1, with the difference that the final calcination was carried out at different temperatures (870° C. and 890° C.) in a continuously operated rotary tube furnace. The rotary tube furnace used had an internal diameter of 12 cm and a length of 2 m and was electrically heated. The residence time of the catalyst extrudants in the rotary tube furnace was on average 15 minutes.

The catalysts K9 and K10 having the nominal composition given in example 1 were obtained. Characterization of the catalysts was carried out as described in example 9. The calcination conditions and the physical properties of the resulting catalysts are summarized in table 2 below.

TABLE 2

Calcination conditions and properties of the catalysts K9 and K10

| Catalyst | Calcination temperature and residence time | Specific surface area $m^2/g$ | Average $CeO_2$ crystallite size nm | K/Fe Mixed oxide phases % | Hematite % |
|---|---|---|---|---|---|
| K9 | 870° C./15 min | 2.0 | 17 | 60 | 18 |
| K10 | 890° C./15 min | 2.1 | 19 | 72 | 7 |

The data from tables 1 and 2 show that not only temperature but also the calcination time or residence time and the type of calcination furnace play a role in setting the content of the K/Fe mixed oxide phases and the average cerium dioxide crystallite size.

Example 12: Dehydrogenation of Ethylbenzene to Styrene at a Steam/Ethylbenzene Ratio of 1.25 kg/kg The catalysts K1 to K10 from examples 1 to 8 and 10 and 11 were used in the dehydrogenation of ethylbenzene to styrene in the presence of steam. The catalyst material obtained was comminuted and sieved, with a fraction of from 0.5 to 0.7 mm being separated off and used for the further experiments.

For each catalyst, two isothermal tube reactors were each filled with 13.3 ml of catalyst of the fraction having a particle size of from 0.5 to 0.7 mm. The reactors were in each case continuously supplied at 620° C. and 1 atm initial pressure with 14.6 g/h of ethylbenzene and 18.3 g/h of deionized (DI) water, corresponding to a water/ethylbenzene (S/HC) ratio of 1.25 kg/kg or 7.36 mol/mol. After stabilization, for instance after 40 hours, samples were taken from the liquid condensate and analyzed by gas chromatography. Conversion, selectivity and styrene yield were determined for each reactor. An average over the two reactors operated in parallel was determined for each catalyst. The results are shown in table 3.

TABLE 3

Catalytic properties of the catalysts K1 to K10 in the conversion of ethylbenzene into styrene at a S/HC ratio of 1.25 kg/kg and 620° C.

| Catalyst | Ethylbenzene conversion [mol %] | Styrene selectivity [mol %] | Styrene yield [mol %] |
|---|---|---|---|
| K1 (comparative example) | 70.5 | 95.6 | 67.4 |
| K2 (comparative example) | 70.3 | 95.6 | 67.2 |
| K3 (comparative example) | 64.1 | 96.7 | 62.0 |
| K4 | 70.8 | 95.5 | 67.6 |
| K5 | 72.8 | 95.1 | 69.2 |
| K6 | 72.2 | 95.1 | 68.7 |
| K7 | 71.4 | 95.7 | 68.3 |
| K8 | 71.3 | 95.3 | 68.0 |
| K9 | 72.7 | 94.9 | 69.0 |
| K10 | 72.4 | 94.8 | 68.6 |

Ethylbenzene conversion, styrene selectivity and yield were determined by means of the following formulae:

$$\text{Conversion(mol \%)} = [A*M_f - B*M_p)/(A*M_f)] \times 100$$

$$\text{Selectivity(mol \%)} = [D*M_p - C*M_f)/(A*M_f - B*M_p)] \times (M_{EB}/M_{ST}) \times 100$$

$$\text{Yield(mol \%)} = \text{Conversion} \times \text{selectivity}/100$$

where:
- A: ethylbenzene concentration at the reactor inlet (% by weight)
- B: ethylbenzene concentration at the reactor outlet (% by weight)
- C: styrene concentration at the reactor inlet (% by weight)
- D: styrene concentration at the reactor outlet (% by weight)
- $M_f$: average molar mass of the organic starting materials
- $M_p$: average molar mass of the organic products
- $M_{EB}$: molar mass of ethylbenzene
- $M_{ST}$: molar mass of styrene The abovementioned figures in respect of concentration and molar masses are in each case based on the organic phase (without water).

The results from table 3 in combination with those from tables 1 and 2 show that both a proportion of K/Fe mixed oxide phases of at least 20% by weight, in particular at least 40% by weight, and a crystallite size of the cerium dioxide particles in the range from 10 to 30 nm, in particular from 14 to 24 nm, are advantageous in order to obtain optimal catalytic performances. For example, the catalyst K1 (comparative example 1) has a comparatively small cerium dioxide particle size but the content of K/Fe mixed oxide phases is less than 20% by weight, and catalyst K1 therefore gives only a comparatively low styrene yield.

On the other hand, the catalysts K2 and K3 (comparative examples 2 and 3) have a high proportion of K/Fe mixed oxide phases but the cerium dioxide crystallites of the catalysts K2 and K3 are too large (greater than 30 nm), and the activity of the catalysts K2 and K3 is therefore comparatively low.

The catalyst K9 from example 9 was calcined at the same temperature as that from comparative example 2, but under different conditions, namely 15 minutes in a continuous rotary tube furnace instead of 1 hour in a stationary muffle furnace. The average crystallite size of the cerium dioxide particles of the catalyst K9 is smaller than that of the catalyst K2, namely 17 nm compared to 38 nm. The catalyst K9 according to the invention has a higher activity than catalyst K2.

The catalyst K5 according to the invention (example 5) (775° C./60 min) was calcined at a lower temperature but for a longer time compared to catalyst K6 (800° C./30 min). Both catalysts display an advantageous activity. Both catalysts have a cerium oxide particle size of 16 nm, but catalyst K5 has a somewhat higher content of K/Fe mixed oxide phases and consequently a somewhat higher activity.

The invention claimed is:

1. A dehydrogenation catalyst comprising
   from 50 to 90% by weight of at least one iron compound, calculated as $Fe_2O_3$;
   from 1 to 30% by weight of at least one potassium compound, calculated as $K_2O$;
   from 2 to 25% by weight of at least one cerium compound, calculated as $CeO_2$;
   from 0.1 to 10% by weight of at least one magnesium compound, calculated as MgO;
   from 0.1 to 10% by weight of at least one calcium compound, calculated as CaO; and
   from 0 to 30% by weight of at least one further component,
   wherein the at least one iron compound and the at least one potassium compound are at least partly present in the form of one or more K/Fe mixed oxide phases of the general formula

$$K_xFe_yO_z,$$

where x is from 1 to 17; y is from 1 to 22 and z is from 2 to 34, where the catalyst comprises at least 40% by weight, based on the total catalyst, of the one or more K/Fe mixed oxide phases and comprises crystalline cerium dioxide having a crystallite size in the range from 16-19 nm.

2. The dehydrogenation catalyst according to claim 1, wherein the catalyst comprises from 0.0001 to 10% by weight of at least one compound selected from compounds encompassing a metal selected from the group consisting of molybdenum, titanium, vanadium and tungsten, calculated as oxide in each case in the highest oxidation state, as further component.

3. The dehydrogenation catalyst according to claim 1, wherein the catalyst comprises
   from 50 to 90% by weight of at least one iron compound, calculated as $Fe_2O_3$;
   from 1 to 30% by weight of at least one potassium compound, calculated as $K_2O$;
   from 2 to 25% by weight of at least one cerium compound, calculated as $CeO_2$;
   from 0.1 to 10% by weight of at least one magnesium compound, calculated as MgO;
   from 0.1 to 10% by weight of at least one calcium compound, calculated as CaO;
   from 0.1 to 10% by weight of at least one molybdenum compound, calculated as $MoO_3$ and
   from 1 to 1000 ppm of at least one titanium compound, calculated as $TiO_2$.

4. The dehydrogenation catalyst according to claim 1, wherein the catalyst comprises at least 60% by weight, based on the total catalyst of the one or more K/Fe mixed oxide phases.

5. The dehydrogenation catalyst according to claim 3, wherein the catalyst comprises at least 60% by weight, based on the total catalyst of the one or more K/Fe mixed oxide phases.

6. A process for producing a dehydrogenation catalyst according to claim 1, which comprises the following steps)
  i) producing a catalyst premix by mixing of at least one iron compound, at least one potassium compound, at least one cerium compound and optionally further metal compounds, optionally further components and optionally at least one binder with a solvent;
  ii) producing shaped catalyst bodies from the catalyst premix obtained in step i); and
  iii) drying of the shaped catalyst bodies and calcinations of the shaped catalyst bodies, where the calcinations of the shaped catalyst bodies is carried out at temperatures of from 700° C. to 850° C. and for a calcination time of from 15 minutes to 90 minutes, as a stationary process; or at temperatures of from 800 to 950° C. and for a calcination time of from 10 minutes to 30 minutes, as a continuous process.

7. The process for producing a dehydrogenation catalyst according to claim 6, wherein the calcination in step iii) is carried out at temperatures of from 700° C. to 850° C. and for a calcination time of from 15 minutes to 90 minutes.

8. The process for producing a dehydrogenation catalyst according to claim 6, wherein the calcination in step iii) is carried out at temperatures of from 800 to 950° C. and for a calcination time of from 10 minutes to 30 minutes.

9. A process for the catalytic dehydrogenation of a hydrocarbon, wherein a mixture of steam and at least one hydrocarbon is brought into contact with a dehydrogenation catalyst according to claim 1.

10. The process for the catalytic dehydrogenation of a hydrocarbon according to claim 9, wherein a mixture of steam and at least one hydrocarbon having a molar steam/hydrocarbon ratio in the range from 1 to 10 is used.

11. The process for catalytic dehydrogenation according to claim 9, wherein the hydrocarbon is ethylbenzene.

\* \* \* \* \*